(12) United States Patent
Chawla et al.

(10) Patent No.: US 9,904,766 B2
(45) Date of Patent: *Feb. 27, 2018

(54) METHOD AND SYSTEM FOR COLLABORATION FOR SHARING PATIENT RECORDS ON LOW COMPUTING RESOURCES ON COMMUNICATION DEVICES

(71) Applicant: Agnity Healthcare, Inc., Fremont, CA (US)

(72) Inventors: Sanjeev Chawla, Fremont, CA (US); Atul Varshneya, Cupertino, CA (US); Amit Kumar, Noida (IN)

(73) Assignee: Agnity Healthcare, Inc., Fremont, CA (US)

(*) Notice: Subject to any disclaimer, the term of this patent is extended or adjusted under 35 U.S.C. 154(b) by 478 days.

This patent is subject to a terminal disclaimer.

(21) Appl. No.: 14/390,754

(22) PCT Filed: Apr. 4, 2013

(86) PCT No.: PCT/US2013/035324
§ 371 (c)(1),
(2) Date: Oct. 3, 2014

(87) PCT Pub. No.: WO2013/152228
PCT Pub. Date: Oct. 10, 2013

(65) Prior Publication Data
US 2015/0120325 A1 Apr. 30, 2015

Related U.S. Application Data

(60) Provisional application No. 61/620,322, filed on Apr. 4, 2012.

(51) Int. Cl.
*G06F 7/04* (2006.01)
*G06F 17/30* (2006.01)
(Continued)

(52) U.S. Cl.
CPC ........ *G06F 19/3425* (2013.01); *G06F 19/322* (2013.01); *G06F 21/6245* (2013.01); *G06Q 50/24* (2013.01); *G06F 15/16* (2013.01); *G06F 17/30* (2013.01); *G06F 19/321* (2013.01); *G06Q 10/00* (2013.01); *G06Q 50/22* (2013.01); *H04N 7/16* (2013.01)

(58) Field of Classification Search
CPC ...... G06F 15/16; G06F 19/321; G06F 19/322; G06F 7/04; G06F 17/30; G06Q 10/00; G06Q 50/22; G06Q 50/24; H04N 7/16
USPC ............................ 705/2; 709/227; 711/100
See application file for complete search history.

(56) References Cited

U.S. PATENT DOCUMENTS 6,302,844 B1 10/2001 Walker et al.
8,112,293 B2 2/2012 Howell et al.
(Continued)

OTHER PUBLICATIONS

International Search Report, International Application No. PCT/US2013/035324 dated Apr. 4, 2013.

*Primary Examiner* — Jayesh Jhaveri
(74) *Attorney, Agent, or Firm* — Arent Fox LLP

(57) ABSTRACT

A method and system are provided for collaboration for sharing patient records on low computing resources on communication devices. The method includes accessing one or more patient data records via a server, where the one or more patient data records are accessed at a first communication device. The method further includes invoking a communication session with one or more second communication devices, where the communication session includes context information of the one or more patient data records. Further, the method includes sending a request to the server, by at least one of the one or more second communication devices, to access the one or more patient data records, where the request includes the context information. Finally, the method includes receiving, at the at least one of the one or more second communication devices, access to the patient data records, where the access is provided during the communication session.

30 Claims, 7 Drawing Sheets

(51) Int. Cl.
*H04N 7/16* (2011.01)
*G06F 19/00* (2018.01)
*G06Q 50/24* (2012.01)
*G06F 21/62* (2013.01)
*G06Q 50/22* (2018.01)
*G06Q 10/00* (2012.01)
*G06F 15/16* (2006.01)

(56) References Cited

U.S. PATENT DOCUMENTS

| | | | |
|---|---|---|---|
| 9,633,404 B2* | 4/2017 | Chawla | G06Q 50/24 |
| 2002/0035485 A1* | 3/2002 | Mita | G06F 19/322 |
| | | | 705/2 |
| 2002/0177757 A1 | 11/2002 | Britton | |
| 2007/0033175 A1* | 2/2007 | Everett-Church | G06F 17/30864 |
| 2007/0061170 A1* | 3/2007 | Lorsch | G06F 19/322 |
| | | | 705/3 |
| 2009/0265185 A1* | 10/2009 | Finn | G06F 19/322 |
| | | | 705/3 |
| 2010/0328320 A1 | 12/2010 | Kerstna et al. | |
| 2011/0009707 A1 | 1/2011 | Kaundinya et al. | |
| 2011/0219419 A1* | 9/2011 | Reisman | G06F 17/30873 |
| | | | 725/112 |
| 2011/0225003 A1* | 9/2011 | McCallie, Jr. | G06Q 10/10 |
| | | | 705/2 |
| 2013/0054481 A1* | 2/2013 | Upadhyaya | G06Q 50/01 |
| | | | 705/319 |

\* cited by examiner

METHOD AND SYSTEM FOR COLLABORATION FOR SHARING PATIENT RECORDS ON LOW COMPUTING RESOURCES ON COMMUNICATION DEVICES

RELATED APPLICATIONS

This present application is a National Stage entry of International Application No. PCT/US2013/035324, filed Apr. 4, 2013, which claims priority to U.S. Provisional Patent Application No. 61/620,322, filed Apr. 4, 2012. The disclosures of the prior applications are incorporated in their entirety reference.

BACKGROUND OF THE INVENTION

1. Field

The present invention relates to sharing patient records in general. More specifically, the present invention relates to methods and systems for collaboration for sharing patient records on low computing resources on communication devices.

2. Description

Collaboration over same files among users is well known in the art. The most popular approach for solutions for such requirements is to use screen sharing along with audio and video conferencing. Examples of such collaboration include, but are not limited to, screen sharing via Skype, Webex and VNC. This is applicable mostly for desktop and laptop computers and is impractical for use on mobile devices with limited computing resources.

Increasingly, mobile devices are becoming the devices of choice for clinicians, for work as well as for personal use such as photo sharing, video sharing, social networking applications and the like. In healthcare Internet Technology (IT) applications, there is a great value in clinicians collaborating around patient information to make care delivery decisions quickly. Proliferation of smartphones is already making it easy for the clinicians to communicate with each other anytime and from anywhere, but it leaves much to be desired with respect to the communication including objective information about the patient—hence a need to be able to share the patient's information along with audio and video communication.

Current systems that manage patient records, such as Electronic Medical Record systems (EMRs) and Electronic Health Record systems (EHRs), do not have an inherent capability to allow audio or video communication concurrently with sharing of patient data records on mobile devices.

Thus it is imperative to have a facility for collaboration for sharing patient records on mobile devices. One of the major challenges for providing collaboration to share patient records on mobile devices is that the mobile devices have limited computing resources. Due to limited computing resources, such devices are not well equipped to support bidirectional screen sharing along with audio and video communications.

In the light of the foregoing discussion, there is a need for a method and system for providing collaboration for sharing patient records, which can be performed using limited computing resources. Thus, there is a need for a method and system that can provide collaboration for sharing patient records using low computing resources on communication devices.

SUMMARY

Accordingly, it is an object of the present invention to provide a method and system for providing collaboration capability for sharing patient records on communication devices.

Accordingly, it is another object of the present invention to provide a method and system for providing collaboration capability for sharing patient records in a secure way on communication devices with limited computing resources.

The above and other objects of the present invention are achieved by providing a method and system for providing collaboration on sharing patient records on communication devices without requiring a lot of computing resources. The method includes accessing one or more patient data records from a server, where the one or more patient data records are accessed on a first communication device. The method further includes invoking a communication session with one or more second communication devices, where the communication session includes context information of the one or more patient data records. Further, the method includes sending a request to the server for accessing the one or more patient data records from at least one of the one or more second communication devices, where the request includes the context information. Finally, the method includes receiving access to the patient data records at the at least one of the one or more second communication devices, where the access is provided during the communication session.

BRIEF DESCRIPTION OF THE DRAWINGS

For a more complete understanding of the present invention, the needs satisfied thereby, and the objects, features, and advantages thereof, reference now is made to the following description taken in connection with the accompanying drawings.

Figure 1:
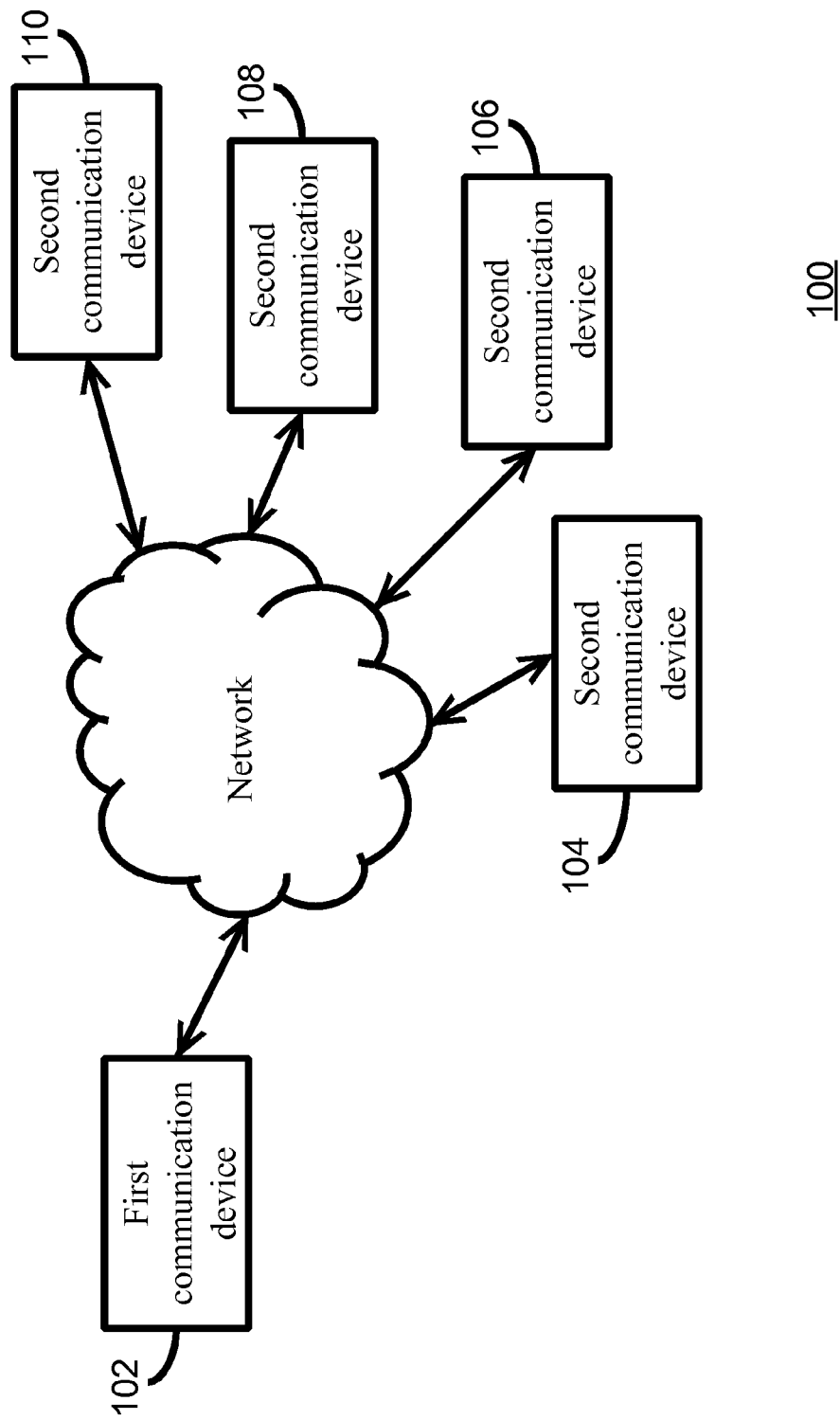
FIG. 1 shows an environment in which various embodiments of the present invention can be practiced.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail the particular method and system for collaboration on communication devices in accordance with an embodiment of the present invention, it should be observed that the present invention resides primarily in combinations of method and system components related to communication device of the present invention.

Accordingly, the system components have been represented where appropriate by conventional symbols in the drawings, showing only those specific details that are pertinent to understanding the present invention so as not to obscure the disclosure with details that will be readily apparent to those of ordinary skill in the art having the benefit of the description herein.

In this document, relational terms such as 'first' and 'second', and the like may be used solely to distinguish one entity or action from another entity or action without necessarily requiring or implying any actual such relationship or order between such entities or actions. The terms 'comprises', 'comprising', or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by 'comprises . . . a' does not, without more constraints, preclude the existence of additional identical elements in the process, method, article, or apparatus that comprises the element.

The terms "computing device" and "communication device" have been used interchangeably, and refer to computing device which has the capability of communicating or interacting with its users.

While the present invention has been described in connection with preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only, with the true scope of the invention indicated by the following claims.

A method is provided for collaboration on a plurality of communication devices, in accordance with an embodiment of the present invention. The method includes accessing one or more patient data records from a server, where the one or more patient data records are accessed on a first communication device. The method further includes invoking a communication session with one or more second communication devices, the communication session including context information of the one or more patient data records. Further, the method includes sending a request to the server for accessing the one or more patient data records from at least one of the one or more second communication devices, the request including the context information. Finally, the method includes receiving access to the patient data records at the at least one of the one or more second communication devices, where the access is provided during the communication session.

In an embodiment of the present invention, the method includes eliminating any need to persistently store the sensitive patient data outside of the clinical information systems such as EMRs, EHRs, and PHRs, that securely manage the patient data. In an embodiment of the present invention, the method includes encrypting the data when in transit over any network.

FIG. 1 shows an environment 100, in which various embodiments of the present invention can be practiced. The environment 100 includes a first communication device 102 and a one or more second communication devices 104, 106, 108 and 110. In the present invention, at least one of the communication devices is a communication device with low computing resources. Examples of the communication devices include, but are not limited to, a mobile phone, a tablet PC, a netbook, an e-book reader, an embedded computing device and a PDA. The first communication device 102 and the one or more second communication devices 104, 106, 108 and 110 are connected via a network. The network is one or more of a 2G network, a 3G network, a 4G network, an internet network, and a local area network (LAN).

Figure 2:
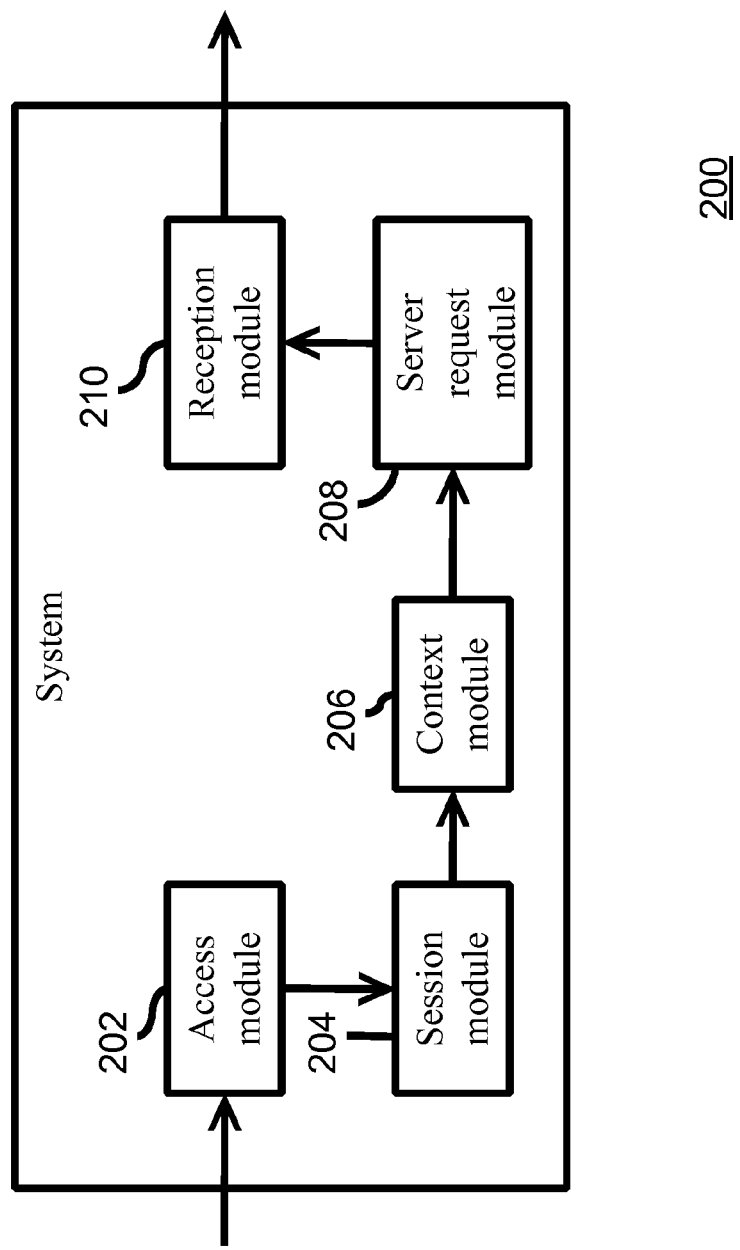
FIG. 2 shows a block diagram of a system for collaboration for sharing patient records on low computing resources on communication devices, in accordance with an embodiment of the present invention.

FIG. 2 shows a block diagram of a system 200 for collaboration for sharing patient records on low computing resources on communication devices, in accordance with an embodiment of the present invention. The system 200 includes an access module 202, a session module 204, a context module 206, a server request module 208 and a reception module 210. The access module 202 accesses one or more patient data records through a server, where the one or more patient data records are accessed on the first communication device 102. The patient data records can include one or more of demographic data, medical history, family history, imaging reports, laboratory test results, medications, dosing, prescription records, surgeries records, vaccination data, observations of daily living (ODLs) and clinical information. Further, the one or more patient records is part of one of an electronic medical record system (EMR), an electronic health record system (EHR) and a personal health record system (PHR).

In an embodiment of the present invention, the server is one of a web server, a server cloud, a proxy server, a local server and a LAN server. Further, the server provides access the one or more patient data records by being one or more of a proxy of the patient data records, an adaptor of the patient data records, and an aggregator of the patient data records. Examples of the patient data records include, but are not limited to, Electronic Medical Record systems (EMRs) and Electronic Health Record systems (EHRs).

The session module 204 then invokes a communication session with the one or more second communication devices 104, 106, 108 and 110, where the communication session is invoked by the first communication device 102. In an embodiment of the present invention, the communication session is one of a voice call and a video call. The communication session takes place using a communication protocol of establishing communication sessions among communication end-points. Examples of the communication protocol include, but are not limited to, Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), Signaling System #7 (SS7), Integrated Services Digital Network (ISDN), Plain Old Telephone Service (POTS) protocol and a voice over Internet Protocol (VoIP) protocol.

The context module 206 sends context information of the one or more patient data records to the one or more second communication devices 104, 106, 108 and 110. In an embodiment of the present invention, the context information is sent by the first communication device 102 to the at least one of the one or more second communication devices 104, 106, 108 and 110 via one or more of a signaling message, a push notification, a multi-media message (MMS), a SMS and an Email. Further, the server request module 208 sends a request to the server for accessing the one or more patient data records from at least one of the one or more second communication devices 104, 106, 108 and 110, where the request includes the context information. In an embodiment of the present invention, the context information includes one or more of a link to the patient data records, a data record ID, authentication information and a session token. Finally, the reception module 210 receives access to the patient data records at the at least one of the one or more second communication devices 104, 106, 108 and 110, where the access includes right to access the one or more patient data records independent of the first communication device 102. For example, the access includes independently scrolling up, scrolling down, scrolling sideways, and going to different page views of the patient data record and the like. In an embodiment of the present invention, the access includes accessing separate patient data records of the one or more patient data records by the first communication device 102 and the at least one of the one or more of second communication devices 104, 106, 108 and 110.

Figure 3:
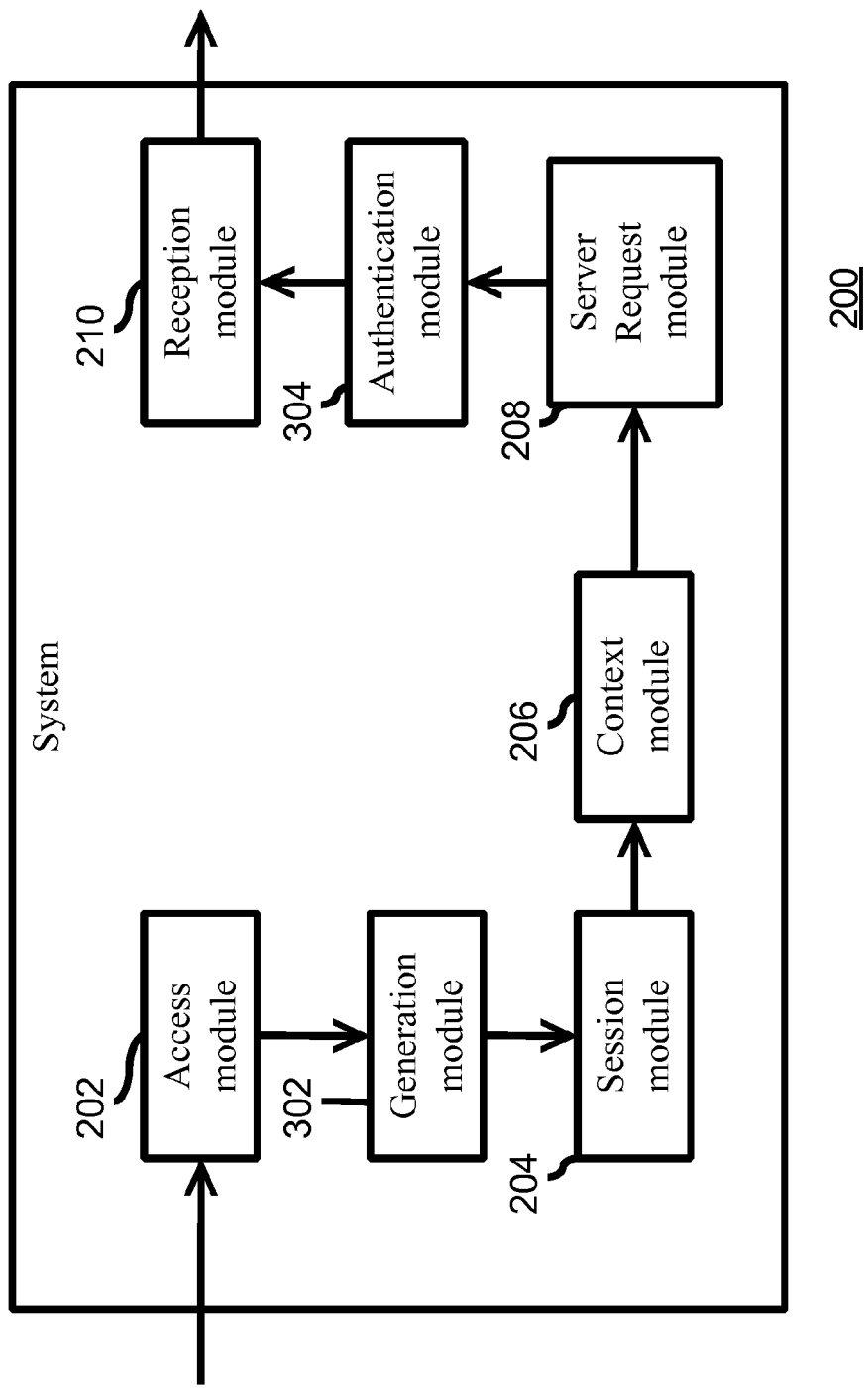
FIG. 3 shows a block diagram of a system for collaboration for sharing patient records on low computing resources on communication devices, in accordance with another embodiment of the present invention.

FIG. 3 shows a block diagram of the system 200 for collaboration for sharing patient data records on low computing resources on communication devices, in accordance with another embodiment of the present invention. The system 200 includes the access module 202, a generation module 302, the session module 204, the context module 206, the server request module 208, an authentication module 304 and the reception module 210. The access module 202 accesses one or more patient data records from a server, where the one or more patient data records are accessed on the first communication device 102. The generation module 302 then generates the context information of the one or more patient data records, where the context information is generated by the server. The server provides the context information to the first communication device 102. Further, the session module 204 invokes a communication session with the one or more second communication devices 104, 106, 108 and 110. The context module 206 then sends context information of the one or more patient data records to the one or more second communication devices 104, 106, 108 and 110. Further, the server request module 208 sends a request to the server for accessing the one or more patient data records from at least one of the one or more second communication devices 104, 106, 108 and 110, where the request includes the context information.

In an embodiment of the present invention, the authentication module 306 authenticates the at least one of the one or more second communication devices 104, 106, 108 and 110 before providing an access to the one or more patient data records, where the authentication is performed by the server. Finally, the reception module 210 receives access to the patient data records at the at least one of the one or more second communication devices 104, 106, 108 and 110, where the access includes right to access the one or more patient data records independent of the first communication device.

In an embodiment of the present invention, the system 200 includes an exit module for closing the access to the one or more patient data records to the at least one of the one or more second communication devices 104, 106, 108 and 110 when the communication session is closed.

In another embodiment of the present invention, the system 200 includes a post-session module for continuing providing the access to the patient data records to the at least one of the one or more second communication devices 104, 106, 108 and 110 after the communication session is closed.

Figure 4:
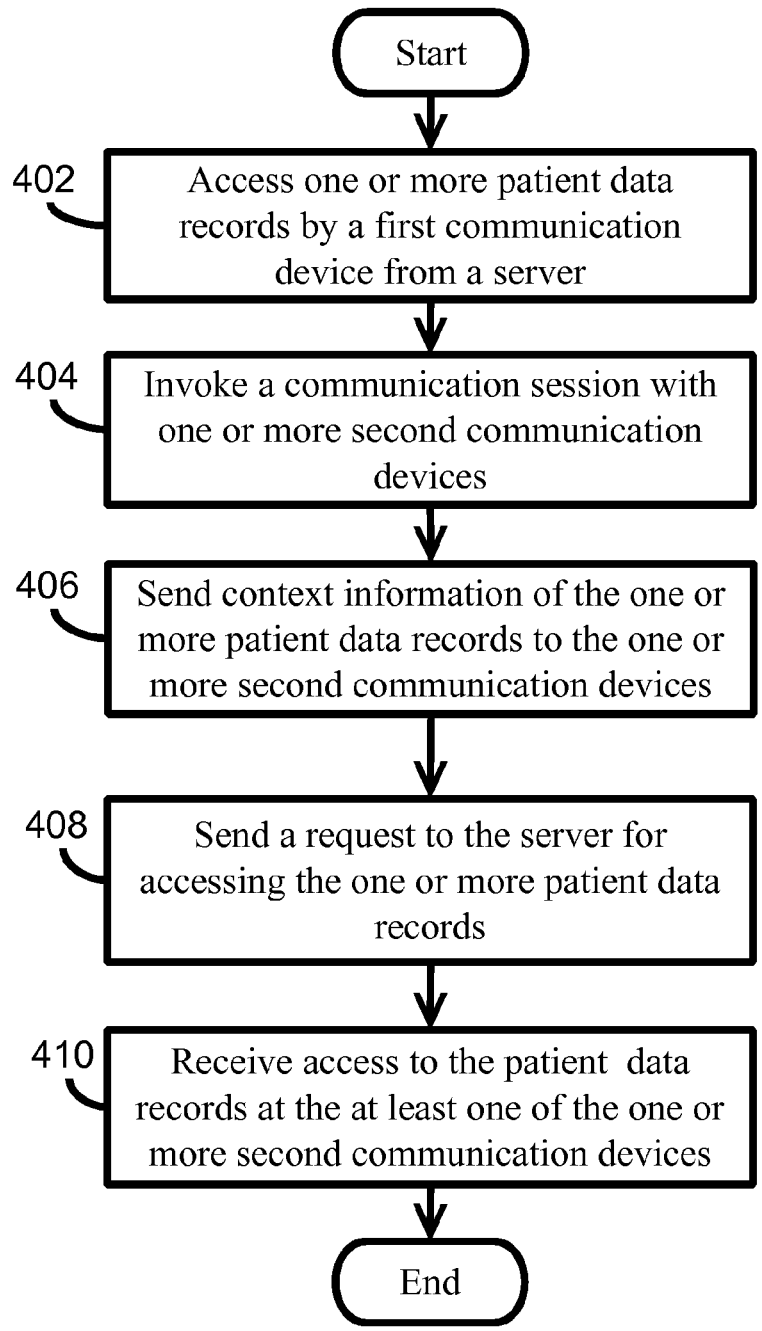
FIG. 4 shows a flow chart of a method for collaboration for sharing patient records on low computing resources on communication devices, in accordance with an embodiment of the present invention.

FIG. 4 shows a flow chart of a method for collaboration for sharing patient records on low computing resources on communication devices, in accordance with an embodiment of the present invention. At step 402, the first communication device 102 accesses one or more patient data records from a server. At step 404, the first communication device 102 invokes a communication session with the one or more second communication devices 104, 106, 108 and 110. In the present embodiment, the communication session includes context information of the one or more patient data records. At step 406, the first communication device 102 sends the context information of the one or more patient data records to the one or more second communication devices 104, 106, 108 and 110. Further, at step 408, at least one of the one or more second communication devices 104, 106, 108 and 110 sends a request to the server for accessing the one or more patient data records, where the request includes the context information. Finally, at step 410, the at least one of the one or more second communication devices 104, 106, 108 and 110 receives access to the one or more patient data records, where the access includes right to access the one or more patient data records independent of the first communication device. For example, the access includes independently scrolling up, scrolling down, scrolling sideways, and going to different page views of the patient data record and the like.

Figure 5:
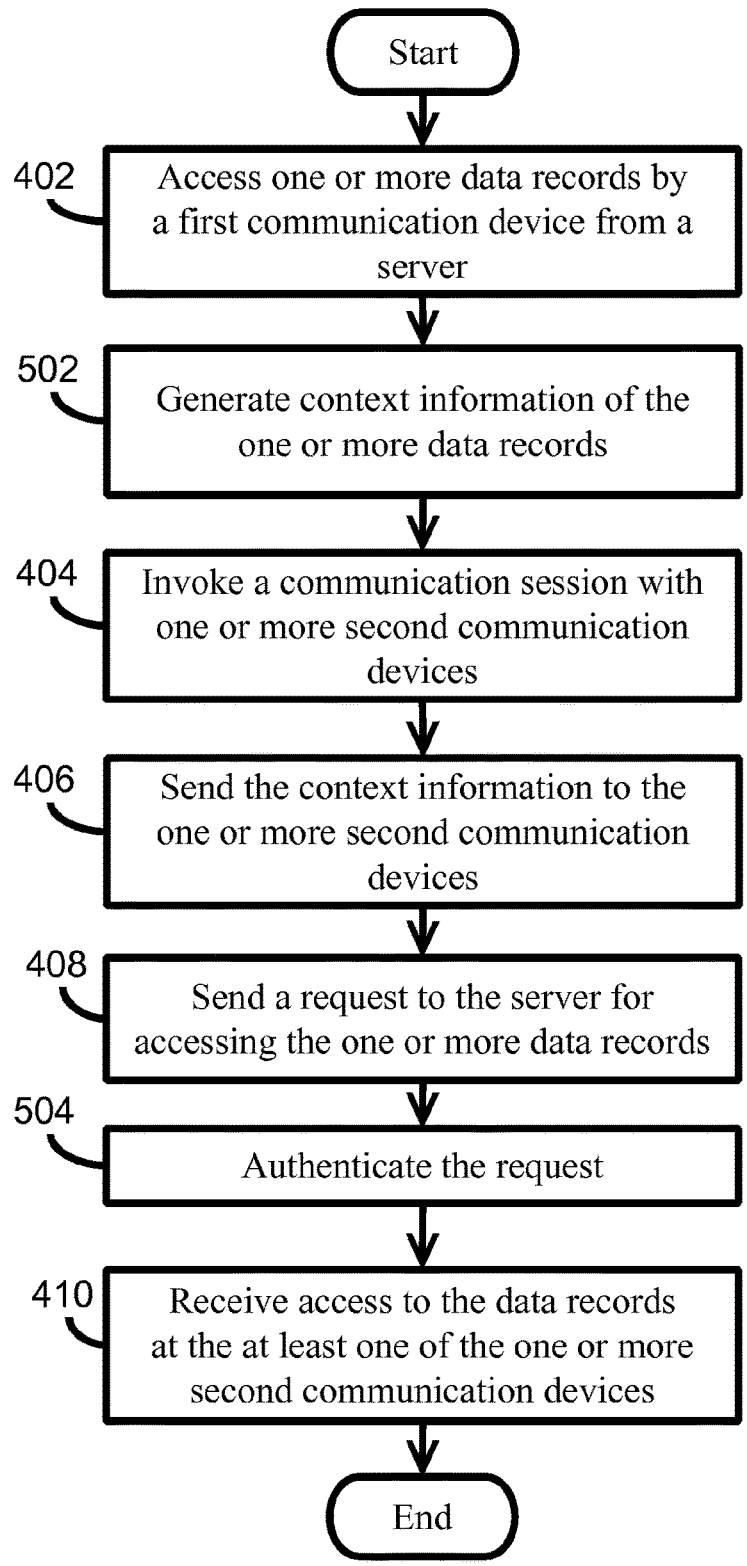
FIG. 5 shows a flow chart of a method for collaboration for sharing patient records on low computing resources on communication devices, in accordance with another embodiment of the present invention.

FIG. 5 shows a flow chart of a method for collaboration for sharing patient records on low computing resources on communication devices, in accordance with another embodiment of the present invention. At step 402, the first communication device 102 accesses one or more patient data records from a server. Further, at step 502, the server generates context information of the one or more patient data records. At step 404, the first communication device 102 invokes a communication session with the one or more second communication devices 104, 106, 108 and 110. In the present embodiment, the communication session includes the context information of the one or more patient data records. At step 406, the context information is sent to the one or more second communication devices. Further, at step 408, at least one of the one or more second communication devices 104, 106, 108 and 110 sends a request to the server for accessing the one or more patient data records, where the request includes the context information. At step 504, the server authenticates the request and checks if the at least one of the one or more communication devices 104, 106, 108 and 110 is authorized to access the one or more patient data records. Finally, at step 410, the at least one of the one or more second communication devices 104, 106, 108 and 110 receives access to the one or more patient data records, where the access includes right to access the one or more patient data records independent of the first communication device.

In an embodiment of the present invention, the system 200 closes the access to the one or more patient data records to the at least one of the one or more second communication devices 104, 106, 108 and 110 when the communication session is closed.

In another embodiment of the present invention, the system 200 continues providing the access to the one or more patient data records to the at least one of the one or more second communication devices 104, 106, 108 and 110 after the communication session is closed.

Figure 6:
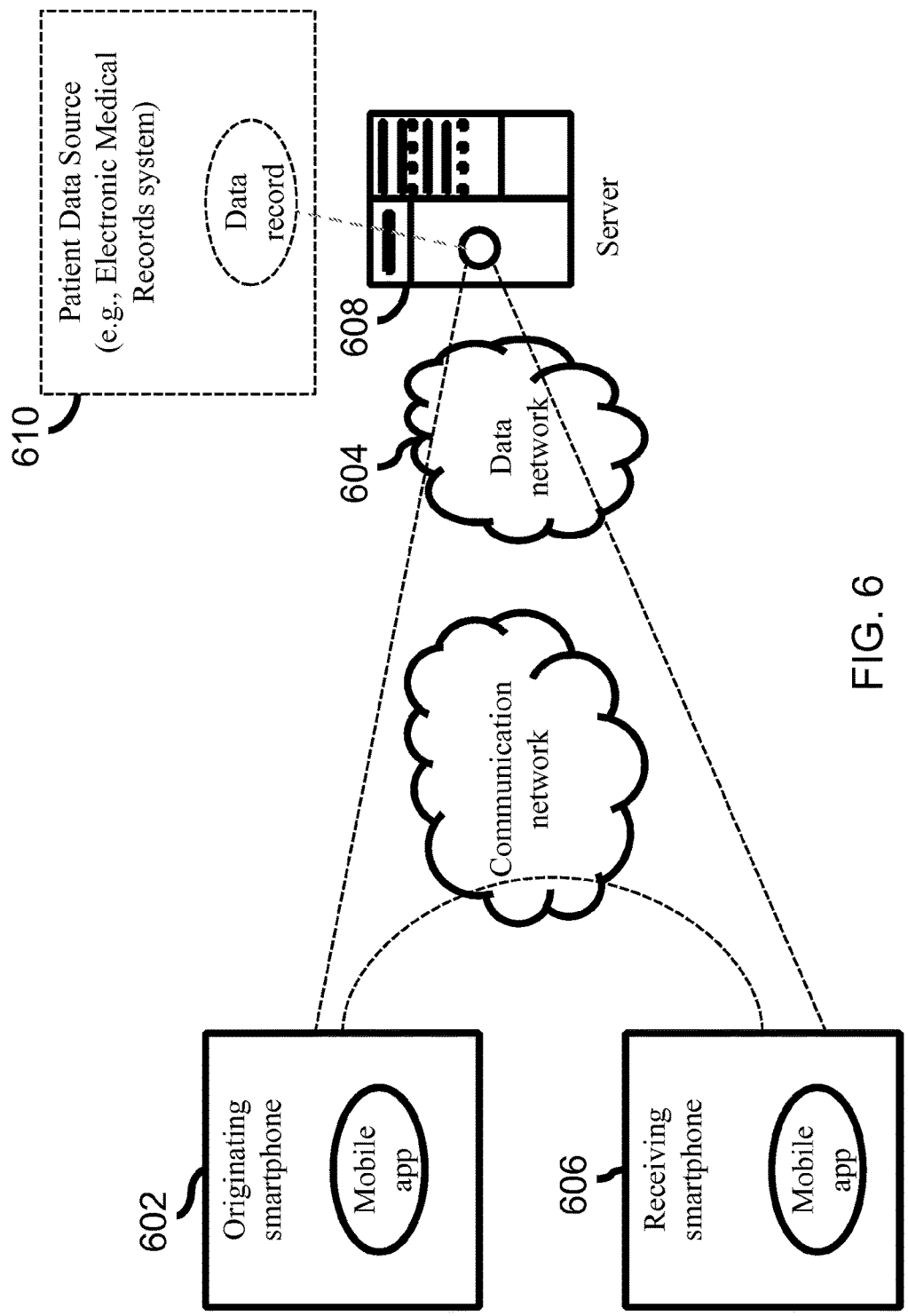
FIG. 6 shows architecture of a system for collaboration for sharing patient records on low computing resources on communication devices, in accordance with an embodiment of the present invention.

FIG. 6 shows architecture of a system for collaboration for sharing patient records on low computing resources on communication devices, in accordance with an embodiment of the present invention. The patient records can be shared between clinicians or between clinicians and patients. An originating smartphone 602 uses the data network 604, to establish media sessions with a receiving smartphone 606. The originating smartphone 602 then accesses a server 608 to look up patient data it needs to share with the receiving smartphone 606. In an embodiment of the present invention, the server 608 is connected to a patient data source repository 610 of the patient data records. Examples of such repositories include, but are not limited to, an electronic medical record system (EMR), an electronic health record system (EHR) and a personal health record system (PHR). In an embodiment of the present invention, the server 608 exchanges data with the patient data source repository 610 using medical data exchange standards. Examples of such standards include, but are not limited to, Health Level Seven (HL7) standards, Electronic Health Record Communication (EN 13606) standards and Health Informatics Service Architecture (HISA) standards. In an embodiment of the present invention, the server 608 is connected to the central repository via secure APIs.

In an embodiment of the present invention, the data exchange between smartphones and the server 608 and the data exchange between the server 608 and the patient data record repository 610 is encrypted. In an embodiment of the present invention, the patient data record repository 610 is never persistently stored on the server 608 or the devices 602 and 606. Examples of the encryption technologies include, but are not limited to, SSL, IPSec and algorithms such as symmetric key cryptography algorithms, public key cryptography algorithms. In an embodiment of the present invention, the server 608 follows Health Insurance Portability and Accountability Act (HIPAA) guidelines for patient privacy and information security, to securely handle the Protected Health Information (PHI). The applications on originating smartphone 602 access the patient data through the server 608 and display to a user. The server 608 authenticates the originating smartphone 602 before providing access to the patient data. The server 608 then interacts with the patient data source repository 610 to provide access to the patient data. The method is designed to specifically eliminate any need for the server 608 and the devices 602 and 608 to store any information that is received from the data source repository 610.

The user then invokes a communication session with the receiving smartphone 606 while the application accesses the patient data from the server 608. The originating smartphone 602 sends location information (context information) of the patient data on the server 608 to the receiving smartphone 606. The communication session, for example protocols like SIP, can carry the context information of the patient data records as part of the signaling fields and/or message headers. The extracted context information is used to fetch the patient data information from the server 608 to display to a user of the receiving smartphone 606. The receiving smartphone 606 then requests the server 608 for the patient data. The server 608 then authenticates the receiving smartphone 606 before providing the data. Once authenticated, the receiving smartphone 606 fetches the patient data from the server 608 and displays to the user of the receiving smartphone 606.

The patient data can be sent from the originating smartphone 602 to the receiving smartphone 606 one after another during the same communication session, thus allowing the users to go through a sequence of patient data records together. The solution allows both the originating smartphone 602 and the receiving smartphone 606 to browse each presented record in their own way independent of the other user. For example, scrolling up, scrolling down, scrolling sideways, and going to different page views of the patient data record and the like.

Figure 7:
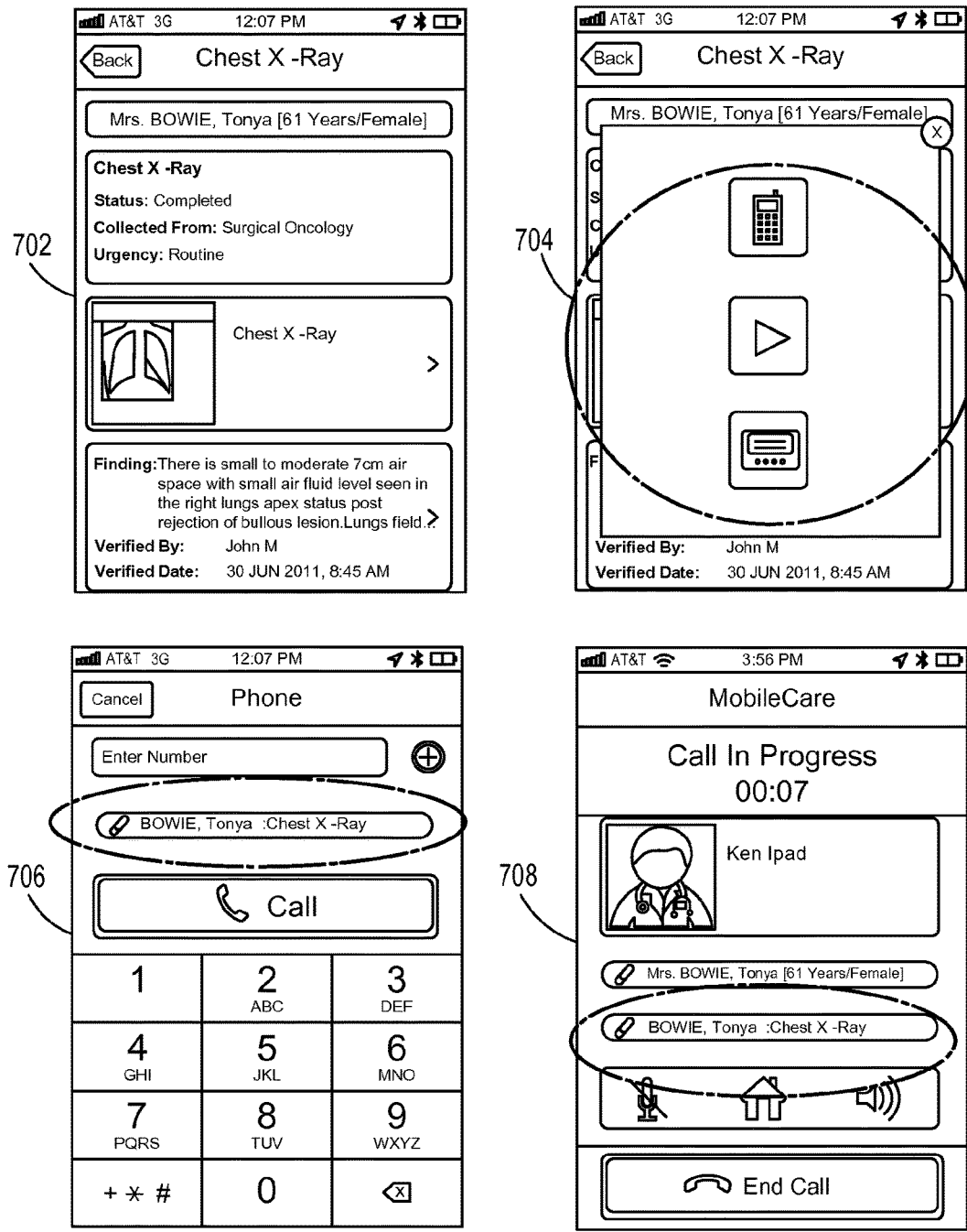
FIG. 7 shows an example of implementation of the method for collaboration for sharing patient records on mobile devices, in accordance with an embodiment of the present invention.

FIG. 7 shows an example of implementation of the method for collaboration for sharing patient records on mobile devices, in accordance with an embodiment of the present invention. At screen 702, an application on user A's device fetches a patient record from the server. The user A can be a clinician or a patient to whom the patient record belongs. The server authenticates the user A before providing access to the patient record. In the present embodiment, the patient record is a Chest X-ray result record. Further, at screen 704, on the application, user A invokes a communication dialog, and selects phone call as the mode of communication. Further, at screen 706, the application records the patient record reference (id and location on the server) and makes it ready for transmission to the other endpoint via the communications signaling protocol. In the present embodiment, the record is shared with a clinician at the other end point. Finally, at screen 708, the record reference is sent via the signaling protocol to the other end point as the phone call is initiated by the application. The device at the other end can then access the patient record, where the access includes right to access the patient data records independent of user A.

In accordance with the present invention, the users using their smartphones, while browsing the patient data records fetched from the server, can initiate any communication session such as audio/video, text messaging, and the like. Via the communication protocol, the context of the data record currently being viewed is passed to the other end. The application on the smartphone at the other end of the communication session extracts this context information, fetches the same record from the server, and presents it to the user for browsing. Thus the users on the two endpoints browse the same data record during the communication session. The patient data records can be sent one after another during the same communication session thus allowing the users to go through a sequence of visuals/patient data records together. The solution allows each user to browse each presented record in their own way independent of the other user—e.g., scrolling up/down/sideways, going to different page views of the data record, among other ways.

Additionally, the invention can be applied to areas where the endpoints are not smartphones, but any devices with small computing power, such as embedded software systems. The present invention brings the voice, video and information based collaboration on such devices by utilizing a different paradigm of the voice, video, data sharing based collaboration. In addition to the streaming of voice and video, it introduces the concept of information collaboration by sharing the context of the information rather than the information itself. So as the users interact via streaming media, they are also able to send context of different pieces of information back and forth among the users. The information itself is available on a server accessible to all the users' devices. The application on the mobile devices automatically fetches the information indexed by the context that it receives from other users and displays it to the user. Thus users are able to have a collaboration session in which they can share any kind of data and be able to discuss it in real-time.

The present invention utilizes the inherent capabilities in communication session signaling to pass on information. This mechanism is leveraged to send context of (link to) data objects managed by a server accessible to both ends of the communication session. Such servers can be deployed in the cloud for global accessibility or the servers can be deployed within an enterprise LAN for secure access to enterprise users only. The server can be a proxy, an adaptor or an aggregator for the data sources, such as applications in the IT infrastructure of the enterprise or publicly accessible services on the Internet.

The present invention is implemented via software routines on the smartphone as well as on the server. The smartphone devices can be running operating systems such as iOS, Android, and Windows. Data communication service such as cellular 3G, 4G, LAN or Wi-Fi has to be available on the smartphone, via which the smartphone and the server can exchange information. The software performs the tasks of initiating media sessions among the smartphones, as well as accessing the data from the server and passing on the location of the data on the server to the receiving smartphone. The server hosts the content which would be shared in the collaboration session.

While the present invention has been described in connection with preferred embodiments, it will be understood by those skilled in the art that variations and modifications of the preferred embodiments described above may be made without departing from the scope of the invention. Other embodiments will be apparent to those skilled in the art from a consideration of the specification or from a practice of the invention disclosed herein. It is intended that the specification and the described examples are considered exemplary only, with the true scope of the invention indicated by the following claims.

What is claimed is:

1. A method for collaboration for sharing patient records on a plurality of communication devices on low computing resources, the method comprising:
   receiving, at a server, a request from a first communication device to access one or more patient data records through the server;
   authenticating, at the server, the first communication device before providing access to the one or more patient data records;
   generating, at the server, context information of the one or more patient data records, wherein the context information is transmitted to the one or more second communication devices during a communication session between the first communication device and the one or more second communication devices;
   receiving a request to access the one or more patient data records by at least one of the one or more second communication devices, the request including the context information extracted from the communication session, wherein the context information is used to access the one or more patient data records on the server;
   authenticating, at the server, the at least one of the one or more second communications devices before providing access to the one or more patient data records;
   providing the at least one of the one or more second communication devices access to the one or more patient data records, the access including a right to access the one or more patient data records independent of the first communication device; and
   facilitating browsing of the one or more patient data records by the first communication device and the at least one of the one or more authenticated second communication devices during the communication session.

2. The method as recited in claim 1, wherein the one or more patient data records comprises one or more of demographic data, medical history, family history, imaging reports, laboratory test results, medications, dosing, prescription records, surgeries records, vaccination data, observations of daily living (ODLs) and clinical information.

3. The method as recited in claim 1, wherein the one or more patient records is part of one of an electronic medical record system (EMR), an electronic health record system (EHR) and a personal health record system (PHR).

4. The method as recited in claim 1, wherein the communication session takes place using a communication protocol.

5. The method as recited in claim 4, wherein the communication protocol is one of Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), Signaling System #7 (SS7), Integrated Services Digital Network (ISDN), Plain Old Telephone Service (POTS) protocol and a voice over Internet Protocol (VoIP) protocol.

6. The method as recited in claim 1, wherein transmitting the context information comprises sending the context information via one or more of a signaling message, a push notification, a multi-media message (MMS), a SMS and an Email.

7. The method as recited in claim 1, wherein the communication devices include one or more of a mobile phone, a tablet PC, a netbook, an e-book reader, an embedded computing device and a PDA.

8. The method as recited in claim 1, wherein the communication session is created over one of Internet, 3G, 4G and local area network (LAN).

9. The method as recited in claim 1, wherein the server is one of a web server, a server cloud, a proxy server, a local server and a LAN server.

10. The method as recited in claim 1, further comprising:
    providing access to the one or more patient data records without storing the one or more patient data records,
    wherein the server comprises one or more of a proxy of the patient data records, an adaptor of the patient data records, and an aggregator of the patient data records.

11. The method as recited in claim 1, wherein the context information comprises one or more of a link to the patient data records, a data record ID, authentication information and a session token.

12. The method as recited in claim 1, further comprising:
    prohibiting access of the at least one of the one or more second communication devices to the one or more patient data records when the communication session is closed.

13. The method as recited in claim 1 further comprising:
    providing continued access of the at least one of the one or more second communication devices to the one or more patient data records after the communication session is closed.

14. A system for collaboration for sharing patient records on a plurality of communication devices on low computing resources, the system comprising: one or more communication devices; and
    a server comprising a computing device, and configured to:

receive a request from a first communication device to access one or more patient data records through the server;
generate context information of the one or more patient data records, wherein the context information is transmitted to the one or more second communication devices during a communication session between the first communication device and the one or more second communication devices;
receive a request to access the one or more patient data records by at least one of the one or more second communication devices, the request including the context information extracted from the communication session, wherein the context information is used to access the one or more patient data records on the server;
authenticate the at least one of the one or more second communications devices before providing access to the one or more patient data records;
provide access to the patient data records, the access including a right to access the one or more patient data records independent of the first communication device; and
facilitate browsing of the one or more patient data records by the first communication device and the at least one of the one or more authenticated second communication devices during the communication session.

15. The system as recited in claim 14, wherein the one or more patient data records comprises one or more of demographic data, medical history, family history, imaging reports, laboratory test results, medications, dosing, prescription records, surgeries records, vaccination data, observations of daily living (ODLs) and clinical information.

16. The system as recited in claim 14, wherein the one or more patient records is part of one of an electronic medical record system (EMR), an electronic health record system (EHR) and a personal health record system (PHR).

17. The system as recited in claim 14, wherein the communication session takes place using a communication protocol.

18. The system as recited in claim 17, wherein the communication protocol is one of Session Initiation Protocol (SIP), Extensible Messaging and Presence Protocol (XMPP), Session Description Protocol (SDP), Inter-Asterisk exchange (IAX), H.323 protocol, Media Gateway Control Protocol (MGCP), Signaling System #7 (SS7), Integrated Services Digital Network (ISDN), Plain Old Telephone Service (POTS) protocol and a voice over Internet Protocol (VoIP) protocol.

19. The system as recited in claim 14, wherein the the context information is transmitted via one of a signaling message, a push notification, a multi-media message (MMS), a SMS and an Email.

20. The system as recited in claim 14, wherein the communication devices include one or more of a mobile phone, a tablet PC, a netbook, an e-book reader, an embedded computing device and a PDA.

21. The system as recited in claim 14, wherein the communication session is created over one of Internet, 3G, 4G and local area network (LAN).

22. The system as recited in claim 14, wherein the server is one of a web server, a server cloud, a proxy server, a local server and a LAN server.

23. The system as recited in claim 14, wherein the server is further configured to provide access to the one or more patient data records without storing the one or more patient data records, the server being one of a proxy of the patient data records, an adaptor of the patient data records, and an aggregator of the patient data records.

24. The system as recited in claim 14, wherein the context information comprises one or more of a link to the one or more patient data records, a data record ID, authentication information and a session token.

25. The system as recited in claim 14, wherein the server is further operable to prohibit access of the at least one of the one or more second communication devices to the one or more patient data records when the communication session is closed.

26. The system as recited in claim 14, wherein the server is further operable to provide continued access of the at least one of the one or more second communication devices to the one or more patient data records after the communication session is closed.

27. A computer program product comprising a non-transitory computer usable medium having control logic stored therein for causing a computer to share patient records on a plurality of communication devices on low computing resources, the control logic comprising:
computer readable program code means for receiving, at a server, a request from a first communication device to access one or more patient data records through the server;
computer readable program code means for authenticating, at the server, the first communication device before providing access to the one or more patient data records;
computer readable program code means for generating, at the server, context information of the one or more patient data records, wherein the context information is transmitted to the one or more second communication devices during a communication session between the first communication device and the one or more second communication devices;
computer readable program code means for receiving a request to access the one or more patient data records by at least one of the one or more second communication devices, the request including the context information extracted from the communication session, wherein the context information is used to access the one or more patient data records on the server;
computer readable program code means for authenticating, at the server, the at least one of the one or more second communications devices before providing access to the one or more patient data records;
computer readable program code means for providing the at least one of the one or more second communication devices access to the patient data records, the access including a right to access the one or more patient data records independent of the first communication device; and
computer readable program code means for facilitating browsing of the one or more patient data records by the first communication device and the at least one of the one or more authenticated second communication devices during the communication session.

28. The method of claim 1, wherein the context information identifies a location of the one or more patient data records on the server.

29. The method of claim 1, further comprising:
receiving, at the server, a request from the first communication device to access a different patient data record through the server;
generating, at the server, context information for the different patient data records, wherein the context information is transmitted to the one or more second communication devices during the communication session between the first communication device and the one or more second communication devices; and receiving a request to access the different patient data record by the at least one of the one or more second communication devices, the request including the context information.

30. The method of claim 1, wherein the context information is extracted from one or more of signaling fields or message headers of the communication session.

\* \* \* \* \*